US006582723B2

(12) United States Patent
Gorsek

(10) Patent No.: US 6,582,723 B2
(45) Date of Patent: Jun. 24, 2003

(54) CANCER IMMUNE COMPOSITION FOR PREVENTION AND TREATMENT OF INDIVIDUALS

(76) Inventor: Wayne F. Gorsek, 7685 Rockford Rd., Boynton Beach, FL (US) 33437

( * ) Notice: Subject to any disclaimer, the term of this patent is extended or adjusted under 35 U.S.C. 154(b) by 69 days.

(21) Appl. No.: 09/847,340

(22) Filed: May 3, 2001

(65) Prior Publication Data

US 2002/0164317 A1 Nov. 7, 2002

(51) Int. Cl.⁷ .............................................. A61K 47/00
(52) U.S. Cl. ....................................... 424/439; 424/400
(58) Field of Search ................................ 424/400, 439

(56) References Cited

U.S. PATENT DOCUMENTS

| 4,289,688 A | 9/1981 | Hotta et al. |
| 4,357,323 A | 11/1982 | Soma et al. |
| 5,437,866 A | 8/1995 | Sun |
| 6,090,615 A | 7/2000 | Nagaoka |
| 6,417,233 B1 * | 7/2002 | Sears et al. .................. 514/549 |

FOREIGN PATENT DOCUMENTS

| JP | 09266766 A | * 10/1997 | ............. A23L/1/28 |

* cited by examiner

Primary Examiner—Thurman K. Page
Assistant Examiner—Charesse Evans

(57) ABSTRACT

An orally ingested composition for prevention, stabilization, reversal and treatment of cancer. Most notably, a nutrient compositions for the treatment of cancer containing omega 3 fatty acids, polysaccharide dietary fibers and coenzyme Q10.

3 Claims, No Drawings

CANCER IMMUNE COMPOSITION FOR PREVENTION AND TREATMENT OF INDIVIDUALS

This application relates to a composition for the prevention, stabilization, reversal and treatment of cancer. An orally ingested composition is provided which contains effective amounts of nutrients which have been demonstrated to provide unique health benefits. The formulation significantly increases immune function thus allowing immune cells to kill cancer cells. The formulation also prevents metastases which is the main reason people die from cancer.

It is an object of the present invention to provide a unique formulation which stops these cancer cells from harming individuals.

SUMMARY OF THE INVENTION

The key to the unique formulation is a combination of specific nutrients that help to prevent, protect and neutralize cancer cells which appear in the body. These nutrients, namely Omega 3 fatty acids such as eicosapentaenoic acid, or docosahexaenoic acid, and optionally, Vitamin E restore immunodeficiency and prolong survival for severely ill patients with general malignancy. Polysaccharide dietary fiber from rice bran(hemicellulose B) with the enzymatic extract of Shiitake mushroom and Coenzyme Q10 (ubiquinone) help regress metastases. The three essential components work together to synergistically prevent and fight malignancy by boosting the body's immune system.

DETAILED DESCRIPTION OF THE INVENTION

Disclosed is an unique formulation that prevents and fights cancer malignancies in the body. The formulation contains three essential ingredients including Omega 3 fatty acids with or without Vitamin E; a polysaccharide dietary fiber from rice bran with the enzymatic extract from the shiitake mushroom; and Coenzyme Q10.

Omega 3 fatty acids (eicosapentaenoic acid or docosahexaenoic acid) in the desired dosage and optionally vitamin E helps restore immunodeficiency and prolong survival for severely ill patients with cancer. The ingredient which is actively incorporated into cell membrane structures appreciably accelerates the differentiation process of the human neoplastic cell.

The second ingredient in the formulation is polysaccharide dietary fiber from rice bran (hemicellulose B) with the enzymatic extract of shiitake mushroom. Formulation dosage ranges from 500 mg to 6,000 mg with the optimal amount being 3000 mg per day.

The third component of the formulation is Coenzyme Q10 (ubiquinone) in a daily dosage range of from 10 mg to 1000 mg per day. The preferred daily dosage being 400 mg. The bioenergetic activity of Coenzyme Q10, expressed as hematological or immunological activity, may be the dominant but not the sole molecular mechanism causing the regression of cancer.

What is claimed is:

1. An orally ingested composition for preventing or treating cancer comprising:
    effective amounts of Omega 3 fatty acids, polysaccharide dietary fiber from rice bran with the enzymatic extract of shiitake mushrooms; and Coenzyme Q10.

2. The orally ingested composition of claim 1, wherein the composition comprises:
    200–6,000 mg Omega 3 fatty acids;
    500–6,000 mg polysaccharide dietary fiber from rice bran with enzymatic extract from shiitake mushrooms; and
    10–1,000 mg Coenzyme Q10.

3. The orally ingested composition of claim 1, wherein the fatty acids further comprise Vitamin E.

* * * * *